US006977257B2

(12) United States Patent
Parab et al.

(10) Patent No.: US 6,977,257 B2
(45) Date of Patent: Dec. 20, 2005

(54) ARIPIPRAZOLE ORAL SOLUTION

(75) Inventors: Prakash V. Parab, Monroe Township, NJ (US); Joyc Tianw i Chou, Fremont, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/131,304

(22) Filed: Apr. 24, 2002

(65) Prior Publication Data

US 2002/0193438 A1 Dec. 19, 2002

Related U.S. Application Data

(60) Provisional application No. 60/286,718, filed on Apr. 25, 2001.

(51) Int. Cl.$^7$ .............................................. A61K 31/496

(52) U.S. Cl. .................................................. 514/253.07

(58) Field of Search ..................................... 514/253.07

(56) References Cited

U.S. PATENT DOCUMENTS

| | | | | |
|---|---|---|---|---|
| 4,734,416 | A | 3/1988 | Banno et al. | 514/253 |
| 5,006,528 | A | 4/1991 | Oshiro et al. | 514/253 |
| 5,686,440 | A | 11/1997 | Kimura et al. | 514/187 |
| 2002/0076437 | A1 * | 6/2002 | Kothari et al. | 424/465 |
| 2003/0077227 | A1 * | 4/2003 | Dugger | 424/43 |

OTHER PUBLICATIONS

Remington's Pharmaceutical Sciences (15$^{th}$ edition) (1975) pp. 201–202; 1254.

* cited by examiner

*Primary Examiner*—Phyllis G. Spivack
(74) *Attorney, Agent, or Firm*—Shah R. Makujina

(57) ABSTRACT

The present invention provides for a pharmaceutical solution suitable for oral administration comprising aripiprazole, a pharmaceutically suitable solvent system, one or more taste-enhancing/masking agents and one or more agents selected from the group consisting of lactic acid, acetic acid, tartaric acid and citric acid, wherein said solution has a pH from 2.5 to 4.5.

13 Claims, No Drawings

ARIPIPRAZOLE ORAL SOLUTION

CROSS REFERENCE TO RELATED APPLICATION

This non-provisional application claims priority from provisional application U.S. Ser. No. 60/286,718 filed Apr. 25, 2001.

FIELD OF THE INVENTION

The present invention relates to pharmaceutical solutions of aripiprazole suitable for oral administration.

BACKGROUND OF THE INVENTION

Schizophrenia is a common type of psychosis characterized by delusions, hallucinations and extensive withdrawal from others. Onset of schizophrenia typically occurs between the age of 16 and 25 and affects 1 in 100 individuals worldwide. It is more prevalent than Alzheimer's disease, multiple sclerosis, insulin-dependent diabetes and muscular dystrophy. Early diagnosis and treatment can lead to significantly improved recovery and outcome. Moreover, early therapeutic intervention can avert costly hospitalization.

Aripiprazole, 7-{4-[4-(2,3-dichlorophenyl)-1-piperazinyl]-butoxy}-3,4-dihydro carbostyril or 7-{4-[4-(2,3-dichlorophenyl)-1-piperazinyl]-butoxy}-3,4-dihydro-2(1H)-quinolinone, is an atypical antipsychotic agent useful for the treatment of schizophrenia U.S. Pat. No. 4,734,416 and U.S. Pat. No. 5,006,528). A pharmaceutical solution of aripiprazole suitable for oral administration can meet the particular needs of patients suffering from schizophrenia who have difficulty swallowing solid oral dosage forms. An oral solution can also provide physicians more flexibility in designing dosage regimens for their patients. The challenges of formulating an oral solution of aripiprazole include solubilizing a sparingly soluble drug using solvents suitable for chronic administration and suitable for administration to both pediatric and geriatric patients while also compensating for a very bitter taste and remaining suitably stable.

SUMMARY OF THE INVENTION

Thus according to a first aspect of the present invention is provided a pharmaceutical solution suitable for oral administration comprising aripiprazole, a pharmaceutically suitable solvent system, one or more taste-enhancing/masking agents and one or more agents selected from the group consisting of lactic acid, acetic acid, tartaric acid and citric acid, wherein said solution has a pH from 2.5 to 4.5.

According to a first embodiment of a second aspect of the present invention is provided a pharmaceutical solution according to the first aspect of the present invention wherein said pH is from 2.5 to 4.0.

According to another embodiment of the second aspect of the present invention is provided a pharmaceutical solution according to the first aspect of the present invention wherein said pH is from 2.8 to 3.8.

According to another embodiment of the second aspect of the present invention is provided a pharmaceutical solution according to the first aspect of the present invention wherein said pH is from 3.0 to 3.6.

According to another embodiment of the second aspect of the present invention is provided a pharmaceutical solution according to the first aspect of the present invention wherein said pH is from 3.1 to 3.3.

According to a first embodiment of a third aspect of the present invention is provided a pharmaceutical solution according to the first aspect of the present invention wherein said agent is lactic acid.

According to another embodiment of the third aspect of the present invention is provided a pharmaceutical solution according to the first aspect of the present invention wherein said agent is acetic acid.

According to another embodiment of the third aspect of the present invention is provided a pharmaceutical solution according to the first aspect of the present invention wherein said agent is tartaric acid.

According to another embodiment of the third aspect of the present invention is provided a pharmaceutical solution according to the first aspect of the present invention wherein said agent is citric acid.

According to another embodiment of the third aspect of the present invention is provided a pharmaceutical solution according to the first aspect of the present invention wherein lactic acid is D-lactic acid According to another embodiment of the third aspect of the present invention is provided a pharmaceutical solution according to the first aspect of the present invention wherein lactic acid is L-lactic acid.

According to another embodiment of the third aspect of the present invention is provided a pharmaceutical solution according to the first aspect of the present invention wherein lactic acid is a mixture of L-lactic acid and D-lactic acid.

According to another embodiment of the third aspect of the present invention is provided a pharmaceutical solution according to the first aspect of the present invention wherein lactic acid is a racemic mixture of L-lactic acid and D-lactic acid.

According to a first embodiment of a fourth aspect of the present invention is provided a pharmaceutical solution according to the first aspect of the present invention wherein said lactic acid is present at concentrations from 0.7 mg /ml to 18 mg/ml.

According to another embodiment of the fourth aspect of the present invention is provided a pharmaceutical solution according to the first aspect of the present invention wherein said lactic acid is present at concentrations from 3.5 mg/ml to 14.5 mg/ml.

According to another embodiment of the fourth aspect of the present invention is provided a pharmaceutical solution according to the first aspect of the present invention wherein said lactic acid is present at concentrations from 5.4 mg/ml to 9 mg/ml.

According to a first embodiment of a fifth aspect of the present invention is provided a pharmaceutical solution according to the first aspect of the present invention wherein aripiprazole is present at concentrations from 0.05 mg /ml to 6 mg/ml.

According to another embodiment of the fifth aspect of the present invention is provided a pharmaceutical solution according to the first aspect of the present invention wherein aripiprazole is present at concentrations from 0.1 mg /ml to 3 mg/ml.

According to another embodiment of the fifth aspect of the present invention is provided a pharmaceutical solution according to the first aspect of the present invention wherein aripiprazole is present at concentrations from 0.25 mg /ml to 2 mg/ml.

According to another embodiment of the fifth aspect of the present invention is provided a pharmaceutical solution according to the first aspect of the present invention wherein aripiprazole is present at concentrations from 0.75 mg/ml to 1.5 mg/ml.

According to another embodiment of the fifth aspect of the present invention is provided a pharmaceutical solution according to the first aspect of the present invention wherein aripiprazole is present at a concentration of 1 mg/ml.

According to a first embodiment of a sixth aspect of the present invention is provided a pharmaceutical solution according to the first aspect of the present invention wherein said pharmaceutically suitable solvent system is comprised of water.

According to another embodiment of a sixth aspect of the present invention is provided a pharmaceutical solution according to the first aspect of the present invention wherein said pharmaceutically suitable solvent system is comprised of water and one or more surfactants.

According to another embodiment of a sixth aspect of the present invention is provided a pharmaceutical solution according to the first aspect of the present invention wherein said pharmaceutically suitable solvent system is comprised of water and one or more solubilizing agents.

According to another embodiment of a sixth aspect of the present invention is provided a pharmaceutical solution according to the first aspect of the present invention wherein said pharmaceutically suitable solvent system is comprised of water, one or more surfactants and one or more solubilizing agents.

According to another embodiment of a sixth aspect of the present invention is provided a pharmaceutical solution according to the first aspect of the present invention wherein said pharmaceutically suitable solvent system is comprised of water and one or more water-miscible solvents.

According to another embodiment of a sixth aspect of the present invention is provided a pharmaceutical solution according to the first aspect of the present invention wherein said pharmaceutically suitable solvent system is comprised of water, one or more water-miscible solvents and one or more surfactants.

According to another embodiment of a sixth aspect of the present invention is provided a pharmaceutical solution according to the first aspect of the present invention wherein said pharmaceutically suitable solvent system is comprised of water, one or more water-miscible solvents and one or more solubilizing agents.

According to another embodiment of a sixth aspect of the present invention is provided a pharmaceutical solution according to the first aspect of the present invention wherein said pharmaceutically suitable solvent system is comprised of water, one or more water-miscible solvents, one or more surfactants and one or more solubilizing agents.

According to another embodiment of the sixth aspect of the present invention is provided a pharmaceutical solution according to other embodiments of the sixth aspect of the present invention wherein said water-miscible solvents are selected from the group consisting of ethanol, glycerin, propylene glycol, sorbitol, polyethylene glycols, polyvinyl pyrrolidone (Povidone) and benzyl alcohol.

According to another embodiment of the sixth aspect of the present invention is provided a pharmaceutical solution according to other embodiments of the sixth aspect of the present invention wherein said water-miscible solvents are selected from the group consisting of glycerin, propylene glycol, LMW polyethylene glycols and sorbitol.

According to another embodiment of the sixth aspect of the present invention is provided a pharmaceutical solution according to other embodiments of the sixth aspect of the present invention wherein said water-miscible solvents are selected from the group consisting of glycerin, propylene glycol and sorbitol.

According to another embodiment of the sixth aspect of the present invention is provided a pharmaceutical solution according to other embodiments of the sixth aspect of the present invention wherein said surfactants are pharmaceutically acceptable surfactants having a hydrophilic-lipophilic balance (HLB) of 15 or above.

According to another embodiment of the sixth of the present invention is provided a pharmaceutical solution according to other embodiments of the sixth aspect of the present invention wherein said surfactants are pharmaceutically acceptable surfactants selected from the group consisting of fatty acid esters, polyoxyethylene fatty acid esters (Sorbitan), polyoxyethylene monoalkyl ethers and poloxamers.

According to another embodiment of the sixth of the present invention is provided a pharmaceutical solution according to other embodiments of the sixth aspect of the present invention wherein said surfactants are pharmaceutically acceptable surfactants selected from the group consisting of TWEEN®, BRIJ® and pluronics (Pluracare®).

According to another embodiment of the sixth aspect of the present invention is provided a pharmaceutical solution according to other embodiments of the sixth aspect of the present invention wherein said pharmaceutically solubilizing agents are selected from the group consisting of povidone and cyclodextrins.

According to another embodiment of the sixth aspect of the present invention is provided a pharmaceutical solution according to other embodiments of the sixth aspect of the present invention wherein propylene glycol, glycerin and water are present in ratios of 0.8–1.2:2.4–3.6:6.4–9.6 w/w respectively.

According to another embodiment of the sixth aspect of the present invention is provided a pharmaceutical solution according to other embodiments of the sixth aspect of the present invention wherein propylene glycol, glycerin and water are present in ratios of 0.9–1.1:2.7–3.3:7.2–8.8 w/w respectively.

According to another embodiment of the sixth aspect of the present invention is provided a pharmaceutical solution according to other embodiments of the sixth aspect of the present invention wherein propylene glycol, glycerin and water are present in a ratio of 1:3:8 w/w respectively.

According to another embodiment of the sixth aspect of the present invention is provided a pharmaceutical solution according to other embodiments of the sixth aspect of the present invention wherein glycerin, propylene glycol and water are present in ratios of 0.8–1.2:2.4–3.6:6.4–9.6 w/w respectively.

According to another embodiment of the sixth aspect of the present invention is provided a pharmaceutical solution according to other embodiments of the sixth aspect of the present invention wherein glycerin, propylene glycol and water are present in ratios of 0.9–1.1:2.7–3.3:7.2–8.8 w/w respectively.

According to another embodiment of the sixth aspect of the present invention is provided a pharmaceutical solution according to other embodiments of the sixth aspect of the present invention wherein glycerin, propylene glycol and water are present in a ratio of 1:3:8 w/w respectively.

According to another embodiment of the sixth aspect of the present invention is provided a pharmaceutical solution according to other embodiments of the sixth aspect of the present invention wherein polyethylene glycol and water are present in ratios of 0.8–1.2:3.2–4.8 w/w respectively.

According to another embodiment of the sixth aspect of the present invention is provided a pharmaceutical solution according to other embodiments of the sixth aspect of the present invention wherein polyethylene glycol and water are present in ratios of 0.9–1.1:3.6–4.4 w/w respectively.

According to another embodiment of the sixth aspect of the present invention is provided a pharmaceutical solution according to other embodiments of the sixth aspect of the present invention wherein polyethylene glycol and water are present in a ratio of 1:4 w/w respectively.

According to another embodiment of the sixth aspect of the present invention is provided a pharmaceutical solution according to other embodiments of the sixth aspect of the present invention wherein polyethylene glycol, propylene glycol and water are present in ratios of 1.6–2.4:0.8–1.2:6.4–8.6 w/w respectively.

According to another embodiment of the sixth aspect of the present invention is provided a pharmaceutical solution according to other embodiments of the sixth aspect of the present invention wherein polyethylene glycol, propylene glycol and water are present in ratios of 1.8–2.2:0.9–1.1:7.2–8.8 w/w respectively.

According to another embodiment of the sixth aspect of the present invention is provided a pharmaceutical solution according to other embodiments of the sixth aspect of the present invention wherein polyethylene glycol, propylene glycol and water are present in a ratio of 2:1:8 w/w respectively.

According to another embodiment of the sixth aspect of the present invention is provided a pharmaceutical solution according to other embodiments of the sixth aspect of the present invention wherein polyethylene glycol, glycerin and water are present in ratios of 1.6–2.4:0.8–1.2:6.4–8.6 w/w respectively.

According to another embodiment of the sixth aspect of the present invention is provided a pharmaceutical solution according to other embodiments of the sixth aspect of the present invention wherein polyethylene glycol, glycerin and water are present in ratios of 1.8–2.2:0.9–1.1:7.2–8.8 w/w respectively.

According to another embodiment of the sixth aspect of the present invention is provided a pharmaceutical solution according to other embodiments of the sixth aspect of the present invention wherein polyethylene glycol, glycerin and water are present in a ratio of 2:1:8 w/w respectively.

According to another embodiment of the sixth aspect of the present invention is provided a pharmaceutical solution according to other embodiments of the sixth aspect of the present invention wherein glycerin and water are present in ratios of 0.8–1.2:6.4–8.6 w/w respectively.

According to another embodiment of the sixth aspect of the present invention is provided a pharmaceutical solution according to other embodiments of the sixth aspect of the present invention wherein glycerin and water are present in ratios of 0.9–1.1:7.2–8.8 w/w respectively.

According to another embodiment of the sixth aspect of the present invention is provided a pharmaceutical solution according to other embodiments of the sixth aspect of the present invention wherein glycerin and water are present in a ratio of 1:8 w/w respectively.

According to another embodiment of the sixth aspect of the present invention is provided a pharmaceutical solution according to other embodiments of the sixth aspect of the present invention wherein polyethylene glycol and water are present in ratios of 1.6–2.4:6.4–8.6 w/w respectively.

According to another embodiment of the sixth aspect of the present invention is provided a pharmaceutical solution according to other embodiments of the sixth aspect of the present invention wherein polyethylene glycol and water are present in ratios of 1.8–2.2:7.2–8.8 w/w respectively.

According to another embodiment of the sixth aspect of the present invention is provided a pharmaceutical solution according to other embodiments of the sixth aspect of the present invention wherein polyethylene glycol and water are present in a ratio of 2:8 w/w respectively.

According to a first embodiment of a seventh aspect of the present invention is provided a pharmaceutical solution according to the first aspect of the present invention wherein said taste-enhancing/masking agents comprise one or more sweeteners.

According to another embodiment of the seventh aspect of the present invention is provided a pharmaceutical solution according to the first embodiment of the seventh aspect of the present invention wherein said taste-enhancing/masking agents comprise one or more flavoring agents.

According to another embodiment of a seventh aspect of the present invention is provided a pharmaceutical solution according to the first aspect of the present invention wherein said taste-enhancing/masking agents comprise one or more sweeteners and one or more flavoring agents.

According to another embodiment of the seventh aspect of the present invention is provided a pharmaceutical solution according to the first embodiment of the seventh aspect of the present invention wherein said sweeteners comprise one or more natural sweeteners.

According to another embodiment of the seventh aspect of the present invention is provided a pharmaceutical solution according to the first embodiment of the seventh aspect of the present invention wherein said sweeteners comprise one or more semi-synthetic sweeteners.

According to another embodiment of the seventh aspect of the present invention is provided a pharmaceutical solution according to the first embodiment of the seventh aspect of the present invention wherein said sweeteners comprise one or more synthetic sweeteners.

According to another embodiment of the seventh aspect of the present invention is provided a pharmaceutical solution according to the first embodiment of the seventh aspect of the present invention wherein said sweeteners comprise one or more natural sweeteners and one or more semi-synthetic sweeteners.

According to another embodiment of the seventh aspect of the present invention is provided a pharmaceutical solution according to the first embodiment of the seventh aspect of the present invention wherein said sweeteners comprise one or more natural sweeteners and one or more synthetic sweeteners.

According to another embodiment of the seventh aspect of the present invention is provided a pharmaceutical solution according to the first embodiment of the seventh aspect of the present invention wherein said sweeteners comprise one or more semi-synthetic sweeteners and one or more synthetic sweeteners.

According to another embodiment of the seventh aspect of the present invention is provided a pharmaceutical solution according to the first embodiment of the seventh aspect of the present invention wherein said sweeteners comprise one or more natural sweeteners, one or more semi-synthetic sweeteners and one or more synthetic sweeteners.

According to another embodiment of the seventh aspect of the present invention is provided a pharmaceutical solution according to the respective embodiment of the seventh aspect of the present invention wherein said natural sweeteners are selected from the group consisting of sucrose, fructose, dextrose, maltose, glucose and glycerin.

According to another embodiment of the seventh aspect of the present invention is provided a pharmaceutical solution according to the respective embodiment of the seventh aspect of the present invention wherein said semi-synthetic sweeteners are selected from the group consisting of lactilol, maltitol, xylitol, sorbitol and mannitol.

According to another embodiment of the seventh aspect of the present invention is provided a pharmaceutical solution according to the respective embodiment of the seventh aspect of the present invention wherein said synthetic sweeteners are selected from the group consisting of saccharin, acesulfame potassium, and aspartame.

According to another embodiment of the seventh aspect of the present invention is provided a pharmaceutical solution according to the respective embodiment of the seventh aspect of the present invention wherein said flavoring agents are selected from the group consisting of cherry, orange, peppermint, strawberry, aniseed, peach, rasberry and orange cream.

According to a first embodiment of an eighth aspect of the present invention is provided a pharmaceutical solution according to the first aspect of the present invention wherein said solution further comprises one or more pharmaceutically acceptable preservatives.

According to another embodiment of a eighth aspect of the present invention is provided a pharmaceutical solution according to the first embodiment of the eighth aspect of the present invention wherein said preservatives comprise one or more anti-microbial preservatives.

According to another embodiment of a eighth aspect of the present invention is provided a pharmaceutical solution according to the first embodiment of the eighth aspect of the present invention wherein said preservatives comprise one or more antioxidants.

According to another embodiment of a eighth aspect of the present invention is provided a pharmaceutical solution according to the first embodiment of the eighth aspect of the present invention wherein said preservatives comprise one or more chelating agents.

According to another embodiment of a eighth aspect of the present invention is provided a pharmaceutical solution according to the first embodiment of the eighth aspect of the present invention wherein said preservatives comprise one or more anti-microbial preservatives and one or more antioxidants.

According to another embodiment of a eighth aspect of the present invention is provided a pharmaceutical solution according to the first embodiment of the eighth aspect of the present invention wherein said preservatives comprise one or more anti-microbial preservatives and one or more chelating agents.

According to another embodiment of a eighth aspect of the present invention is provided a pharmaceutical solution according to the first embodiment of the eighth aspect of the present invention wherein said preservatives comprise one or more antioxidants and one or more chelating agents.

According to another embodiment of a eighth aspect of the present invention is provided a pharmaceutical solution according to the first embodiment of the eighth aspect of the present invention wherein said preservatives comprise one or more anti-microbial preservatives, one or more antioxidants and one or more chelating agents.

According to another embodiment of an eighth aspect of the present invention is provided a pharmaceutical solution according to the respective embodiment of the eighth aspect of the present invention wherein said anti-microbial preservatives are selected from the group consisting of methylparaben, ethylparaben, propylparaben, butylparaben, benzoic acid, sodium benzoate, benzyl alcohol, sorbic acid and potassium sorbate.

According to another embodiment of a eighth aspect of the present invention is provided a pharmaceutical solution according to the respective embodiment of the eighth aspect of the present invention wherein said antioxidants are selected from the group consisting of sodium metabisulfite, sodium bisulfite, propyl gallate, sodium ascorbate and ascorbic acid.

According to another embodiment of an eighth aspect of the present invention is provided a pharmaceutical solution according to the respective embodiment of the eighth aspect of the present invention wherein said chelating agents are selected from the group consisting of disodium EDTA, tartaric acid, malic acid and citric acid.

According to a ninth aspect of the present invention is provided a pharmaceutical solution of the first embodiment of the first aspect of the present invention wherein said solution is substantially devoid of suspended particles.

Other embodiments of the invention provide a pharmaceutical solution according to two or more of the embodiments described herein suitably combined.

Yet other embodiments of the invention will be apparent according to the description provided below.

DETAILED DESCRIPTION OF THE INVENTION

Unless otherwise indicated, "lactic acid" as used herein includes D-lactic acid, L-lactic acid and/or mixtures thereof.

Non-limiting examples of suitable preparations of the present invention are provided hereinbelow.

EXAMPLE ONE

TABLE 1

Example One Oral Solution

| Ingredients | mg/mL |
|---|---|
| Aripiprazole | 1.0 |
| PEG-400 | 125 |
| DL-Lactic acid | 8.47 |
| Sodium hydroxide* | 0.45 (1) |
| Benzoic acid | 1.5 |
| Sucrose | 360 |
| Fructose | 350 |
| Natural orange cream flavor | 3.0 |
| Purified Water | QS |

(1) The exact amount of sodium hydroxide shown may be varied to adjust pH of batch solution to between 3.1 and 3.2.

1. Charge the batching vessel with PEG-400 and a portion (80–90%) of purified water. With continuous moderate agitation, add the DL-lactic acid to the batching vessel and mix until dissolved.
2. With continuous moderate agitation, add aripiprazole to the batching vessel from Step 1 and mix. Verify by visual inspection that all powder has dissolved
3. With continuous moderate agitation, add sodium hydroxide 2.5 N solution to adjust the pH of the batch from Step 3 to between 3.1 and 3.2.

4. With continuous moderate agitation, heat the batch from Step 3 to 45–55° C. Then add benzoic acid while maintaining temperature between 45–55° C. Verify by visual inspection that all powder has dissolved.
5. Reduce temperature of the batch from Step 4 to 40–50° C., add sucrose and fructose and mix. Verify by visual inspection that all powder has dissolved
6. With continuous moderate agitation, cool the solution from Step 5 to 25–30° C.
7. With continuous moderate agitation, add flavor to the solution from Step 6 and mix.
8. With continuous moderate agitation, add sufficient amount of purified water to the batch from Step 7 to adjust to the final batch size and mix.
9. Filter the solution from Step 8 through a stainless steel screen.
10. Store the solution from Step 9 in a tank.

EXAMPLE TWO

TABLE 2

Example Two Oral Solution

| Ingredients | mg/mL |
|---|---|
| Aripiprazole (at 100% purity) | 1.0 |
| Glycerin, USP/EP/BP | 150.0 |
| DL-Lactic Acid, USP/EP | 8.47 |
| Sodium Hydroxide, NF/EP/BP | 0.45 (1) |
| Propylene Glycol, USP/EP | 50.0 |
| Methylparaben, NF/BP/EP | 1.8 |
| Propylparaben, NF/BP/EP | 0.2 |
| Sucrose, NF/BP/EP | 400.0 |
| Fructose, USP/EP/BP | 200.0 |
| Natural Orange Cream Flavor WONF (2) | 3.0 |
| Purified Water USP/EP | q.s. |

(1) The exact amount of sodium hydroxide shown may be varied to adjust pH of batch solution to between 3.1 and 3.2.
(2) WONF means With Other Natural Flavors.

1. Charge the batching vessel with glycerin and a portion (80–90%) of purified water. With continuous moderate agitation, add the DL-lactic acid and a portion of propylene glycol to the batching vessel and mix until dissolved.
2. In a container, disperse methylparaben and propylparaben in a portion of propylene glycol and mix.
3. With continuous moderate agitation, add aripiprazole to the batching vessel from Step 1 and mix. Verify by visual inspection that all powder has dissolved
4. With continuous moderate agitation, add sodium hydroxide 2.5 N solution to adjust the pH of the batch from Step 3 to between 3.1 and 3.2.
5. With continuous moderate agitation, heat the batch from Step 4 to 45–55° C. Then add the parabens and propylene glycol mixture from Step 2 to the batching vessel and mix while maintaining temperature between 45–55° C. Verify by visual inspection that all powder has dissolved.
6. Reduce temperature of the batch from Step 5 to 40–50° C., add sucrose and fructose and mix. Verify by visual inspection that all powder has dissolved
7. With continuous moderate agitation, cool the solution from Step 6 to 25–30° C.
8. With continuous moderate agitation, add flavor to the solution from Step 7 and mix.
9. With continuous moderate agitation, add sufficient amount of purified water to the batch from Step 8 to adjust to the final batch size and mix.
10. Filter the solution from Step 9 through a stainless steel screen.

What is claimed is:

1. A pharmaceutical solution suitable for oral administration comprising aripiprazole, a pharmaceutically suitable solvent system comprised of one or more agents selected from the group consisting of water, ethanol, glycerin, propylene glycol and sorbitol, one or more taste-enhancing/masking agents and one or more other agents selected from the group consisting of lactic acid, acetic acid, tartaric acid and citric acid, wherein said solution has a pH from 2.5 to 4.0.

2. A pharmaceutical solution according to claim 1 wherein said other agent is lactic acid.

3. A pharmaceutical solution according to claim 2 wherein said lactic acid is present at concentrations selected from the group of ranges consisting of 0.7 mg/ml to 18 mg/ml, 3.5 mg/ml to 14.5 mg/ml and 5.4 mg/ml to 9 mg.

4. A pharmaceutical solution according to claim 1 wherein aripiprazole is present at concentrations selected from the group of ranges consisting of 0.05 mg/ml to 6 mg/ml, 0.1 mg/ml to 3 mg/ml, 0.25 mg/ml to 2 mg/ml and 0.75 mg/ml to 1.5 mg/ml.

5. A pharmaceutical solution according to claim 1 wherein said pharmaceutically suitable solvent system is comprised of propylene glycol, glycerin and water each being present in ratios of 0.8–1.2:2.4–3.6:6.4–9.6 w/w respectively.

6. A pharmaceutical solution according to claim 1 wherein said pharmaceutically suitable solvent system is comprised of glycerin, propylene glycol and water each being present in ratios of 0.8–1.2:2.4–3.6:6.4–9.6 w/w respectively.

7. A pharmaceutical solution according to claim 1 wherein said pharmaceutically suitable solvent system is comprised of glycerin and water each being present in ratios of 0.8–1.2:6.4–8.6 w/w respectively.

8. A pharmaceutical solution according to claim 1 wherein said pharmaceutically suitable solvent system is comprised of glycerin and water each being present in ratios of about 1:3 w/w respectively.

9. A pharmaceutical solution according to claim 1 further comprising disodium EDTA.

10. A pharmaceutical solution suitable for oral administration comprising aripiprazole, a pharmaceutically suitable solvent system, one or more taste-enhancing/masking agents and lactic acid, wherein said solution has a pH from 2.5 to 4.5.

11. A pharmaceutical solution according to claim 10 wherein said pharmaceutically suitable solvent system is comprised of one or more agents selected from the group consisting of water, ethanol, glycerin, propylene glycol and sorbitol and wherein said solution has a pH from 2.5 to 4.0.

12. A pharmaceutical solution according to claim 11 wherein one or more of said taste-enhancing/masking agents are selected from the group consisting of flavoring agents, sucrose, fructose, dextrose, maltose, glucose, maltitol, xylitol, sorbitol and mannitol.

13. A pharmaceutical solution suitable for oral administration comprising aripiprazole, glycerin, lactic acid, propylene glycol, methylparaben, propylparaben, sucrose, fructose and water.

* * * * *

UNITED STATES PATENT AND TRADEMARK OFFICE

CERTIFICATE OF CORRECTION

PATENT NO. : 6,977,257 B2 Page 1 of 1
DATED : December 20, 2005
INVENTOR(S) : Parab, Prakash V. et al.

It is certified that error appears in the above-identified patent and that said Letters Patent is hereby corrected as shown below:

Title page,
Item [75], Inventors, change "Joyc Tianw i Chou" to -- Joyce Tianwei Chou --.

Signed and Sealed this

Eleventh Day of April, 2006

JON W. DUDAS
*Director of the United States Patent and Trademark Office*